(12) United States Patent
Kwon et al.

(10) Patent No.: US 8,485,720 B2
(45) Date of Patent: Jul. 16, 2013

(54) MEASUREMENT METHOD OF DISTINGUISHING DEW AND FROST POINT USING QUARTZ CRYSTAL MICROBALANCE DEW-POINT SENSOR IN LOW TEMPERATURE

(75) Inventors: Su Yong Kwon, Daejeon (KR); Jong Chul Kim, Daejeon (KR); Byung Il Choi, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 354 days.

(21) Appl. No.: 12/747,320

(22) PCT Filed: Dec. 26, 2007

(86) PCT No.: PCT/KR2007/006830
§ 371 (c)(1),
(2), (4) Date: Sep. 7, 2010

(87) PCT Pub. No.: WO2009/088108
PCT Pub. Date: Jul. 16, 2009

(65) Prior Publication Data
US 2010/0322280 A1    Dec. 23, 2010

(30) Foreign Application Priority Data
Dec. 14, 2007  (KR) .................. 10-2007-0131458

(51) Int. Cl.
*G01N 25/06* (2006.01)
*G01K 11/06* (2006.01)
*H03B 11/00* (2006.01)

(52) U.S. Cl.
USPC .................. 374/28; 374/117; 374/16; 73/73; 331/70; 331/158

(58) Field of Classification Search
USPC ................ 374/16–17, 19–20, 22, 27–28, 11, 374/12, 10, 117–119, 14–15, 7, 100, 208; 331/70, 23, 107 R, 187, 158; 73/73, 29.01, 73/29.02, 335.02, 335.03, 61.45, 61.49, 61.75, 73/61.76, 61.79
See application file for complete search history.

(56) References Cited

U.S. PATENT DOCUMENTS 4,760,351 A * 7/1988 Newell et al. .................... 331/48
4,793,182 A * 12/1988 Djorup ........................ 73/335.02

(Continued)

FOREIGN PATENT DOCUMENTS

JP       56126738 A     10/1981
JP        5746147 A      3/1982

(Continued)

*Primary Examiner* — Gail Verbitsky
(74) *Attorney, Agent, or Firm* — The Webb Law Firm

(57) ABSTRACT

The present invention relates to a measurement method of dew-point in low temperature, and more specifically to a measurement method of accurately distinguishing dew-point and frost-point using a quartz crystal microbalance dew-point sensor in a low temperature of 0° C. or less. To this end, the present invention provides a measurement method of distinguishing dew and frost point using a quartz crystal microbalance dew-point sensor in low temperature, comprising the steps of: measuring a resonant frequency of a quartz crystal microbalance dew-point sensor while slowly dropping temperature; observing shock waves of the resonant frequency; and determining dew point or frost point through the observation of the resonant frequency and shock waves of the quartz crystal microbalance dew-point sensor.

8 Claims, 4 Drawing Sheets

U.S. PATENT DOCUMENTS

| | | | |
|---|---|---|---|
| 5,460,450 A * | 10/1995 | Buck | 374/20 |
| 5,661,233 A * | 8/1997 | Spates et al. | 73/61.45 |
| 6,073,479 A | 6/2000 | Shapiro et al. | |
| 6,126,311 A | 10/2000 | Schuh | |
| 6,926,439 B2 * | 8/2005 | Zlochin | 374/20 |
| 8,196,451 B2 * | 6/2012 | Konno et al. | 73/24.06 |
| 8,215,171 B1 * | 7/2012 | Smith et al. | 73/580 |
| 2012/0013410 A1 * | 1/2012 | Rebel et al. | 331/70 |

FOREIGN PATENT DOCUMENTS

| | | | |
|---|---|---|---|
| JP | 02019742 A | * | 1/1990 |
| JP | 07260661 A | * | 10/1995 |
| RU | 106395 U1 | * | 7/2011 |
| SU | 651271 A | * | 3/1979 |
| SU | 682854 B | * | 8/1979 |

* cited by examiner

MEASUREMENT METHOD OF DISTINGUISHING DEW AND FROST POINT USING QUARTZ CRYSTAL MICROBALANCE DEW-POINT SENSOR IN LOW TEMPERATURE

TECHNICAL FIELD

The present invention relates to a measurement method of dew-point in low temperature, and more specifically to a measurement method of accurately distinguishing dew-point and frost-point using a quartz crystal microbalance dew-point sensor in a low temperature of 0° C. or less.

BACKGROUND ART

A humidity measurement is very important in many fields such as environment, food, agriculture, medical care, automobile, textile, semiconductor technology, bio technology, and the like. To this end, various humidity measurement technologies using impedance, capacitance, optical method, surface acoustic wave, etc. have been developed. In the humidity measurement, the dew-point measurement has been generally used as a standard method and the dew-point sensor in a chilled mirror type has been currently used as a standard calibrator in many laboratories.

In fields such as semiconductor, display, ultrapure gas manufacture, etc., a plurality of processes has been performed in very low pressure or vacuum environment. In the case of a semiconductor process, although there is an extremely small amount of moisture in a portion of remained gas during the process, the moisture has a large effect on physical properties of a metal and a semiconductor thin film. Further, since an extremely small amount of moisture causes the same defects even in the case of the display process, a need exists for a technology capable of measuring an extremely small amount of moisture such as ppm and ppb within a minimum space.

Therefore, a need for a technology capable of accurately measuring and analyzing the dew point in a low humidity environment has been increased. A currently commercialized dew-point measurement apparatus can measure the dew point up to −90° C., but is difficult to accurately measure supercooled dew point due to low accuracy in low temperature.

As one example, in the case of the dew-point measurement apparatus in the currently generally used chilled mirror type, since it measures a formation of the dew point by means of the optical method, the measurement apparatus can perform the dew-point measurement only the case where a dew of 3 µg/cm² or more is produced. Also, when measuring the dew point in a low temperature between 0° C. and −40° C., liquid dew may be produced, but solid frost may be produced. However, it is not easy to distinguish them. The temperature of the dew point (or frost point) measured according to whether water drop produced in 0° C. or less is the liquid dew or the solid frost has a large error (about 4° C.) so that the accurate measurement may not be performed. Many methods to remove such an error have been studied; however, many solutions have been currently required.

DISCLOSURE

Technical Problem

An object of the present invention provides a new method of recognizing a supercooled dew point using a quartz crystal microbalance dew-point sensor and provides a dew-point measurement method of accurately distinguishing supercooled dew point and frost point in a low temperature of 0° C. or less.

Also, another object of the present invention provides a dew-point measurement method of accurately distinguishing dew point, supercooled dew point and frost point by scanning once resonant frequency using a quartz crystal microbalance dew-point sensor in a low temperature, without adding a new system.

Technical Solution

In order to accomplish the aforementioned technical problem, the measurement method of distinguishing dew and frost point using a quartz crystal microbalance dew-point sensor in low temperature comprises the steps of: measuring a resonant frequency of a quartz crystal microbalance dew-point sensor while slowly dropping temperature; observing shock waves of the resonant frequency; and determining dew point or frost point through the observation of the resonant frequency and shock waves of the quartz crystal microbalance dew-point sensor.

When observing the resonant frequency of a quartz resonator in the quartz crystal microbalance dew-point sensor while dropping temperature, it is judged that the temperature is the dew point if a transition phenomenon of the shock wave and the resonant frequency is observed in a resonant frequency pattern of the quartz resonator and the temperature is the frost point if the transition phenomenon of the shock wave and the resonant frequency is not observed, The quartz crystal microbalance dew-point sensor may be configured of a quartz resonator, a Peltier cooler device, a quartz resonator holder, and a platinum resistance temperature sensor.

Slowly dropping the temperature is performed by controlling the temperature of the quartz resonator using the Peltier cooler device and the temperature dropped by means of the Peltier cooler device is transferred to the quartz resonator through the quartz resonator holder so that the temperature of the quartz resonator can be controlled.

The quartz resonator holder is made of copper and one surface of the quartz resonator holder may be attached with the platinum resistance temperature sensor to measure the temperature of the quartz resonator holder.

The resonant frequency of the quartz resonator is transferred to a computer via a coaxial cable and may be stored as a function of temperature by means of the computer.

Advantageous Effects

The measurement method of dew point in low temperature according to the present invention has an advantage capable of accurately distinguishing and measuring three waterdrop forms, that is, frost, supercooled dew, and dew, using a quartz crystal microbalance dew-point sensor.

Furthermore, it has an effect that the measurement method can confirm supercooled dew point in low temperature due to a characteristic frequency phenomenon of the quartz resonator and can accurately measure supercooled dew point and frost point by scanning once resonant frequency without having a further apparatus

DESCRIPTION OF DRAWINGS

The above and other objects, features and advantages of the present invention will become apparent from the following description of preferred embodiments given in conjunction with the accompanying drawings, in which.

BEST MODE

Figure 1:
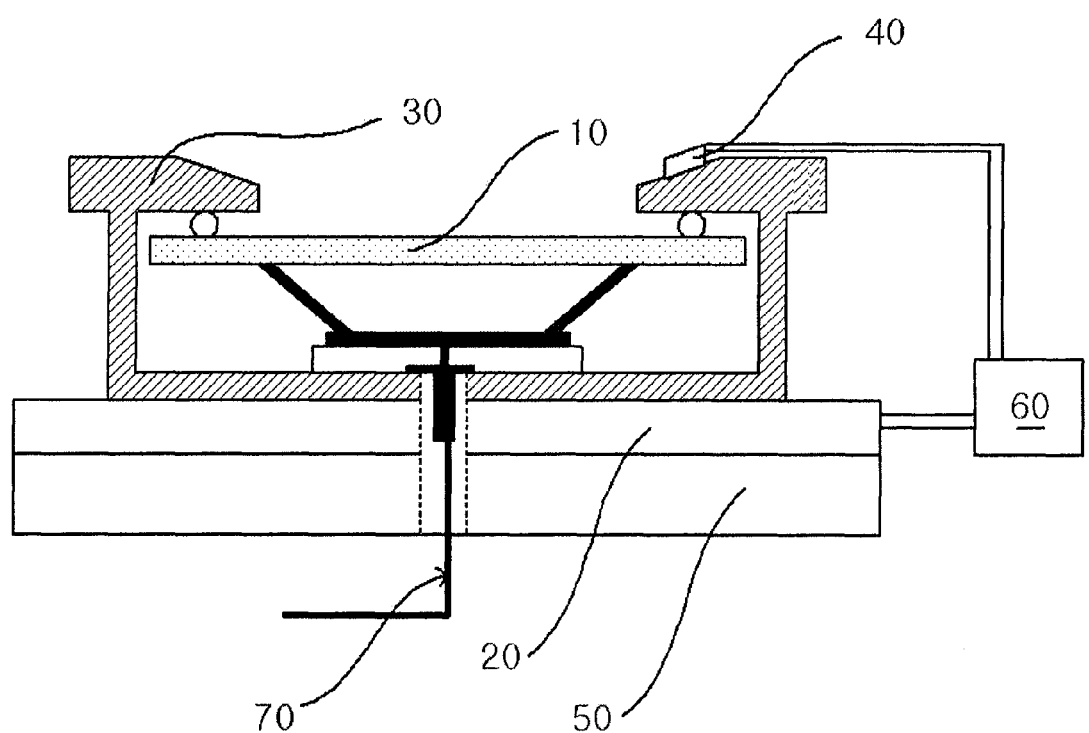
FIG. 1 is a cross-sectional view of a quartz crystal microbalance dew-point sensor.

Hereinafter, the embodiments of the present invention will be described in detail with reference to accompanying drawings. The following described embodiments are provided, by way of example, so as to fully transfer the idea of the present invention to those skilled in the art. Therefore, the present invention is not limited to the embodiments described below and can be embodied in other forms. And, in the drawings, a length, a thickness, and the like of a layer and a region can be emphasized for convenience of explanation. Like reference numerals refer to like components throughout the specification.

FIG. 1 is a cross-sectional view of a quartz crystal microbalance dew-point sensor according to the present invention. The measurement technology of distinguishing dew and frost point using the quartz crystal microbalance dew-point sensor in low temperature will be described below with reference to the cross-sectional view of the quartz crystal microbalance dew-point sensor.

Referring to the drawings, the resonant frequency of the quartz crystal microbalance dew-point sensor is measured while slowly dropping temperature of quartz resonator in the quartz crystal microbalance dew-point sensor. The quartz crystal microbalance dew-point sensor may be configured of a quartz resonator 10, a Peltier cooler device 20, a quartz resonator holder 30, and a platinum resistance temperature sensor 40.

Slowly dropping the temperature of the quartz crystal microbalance dew-point sensor may be performed by controlling the temperature of the quartz resonator 10 using the Peltier cooler device 20. Concretely describing, the Peltier cooler device 20 is positioned to be contacted to a bottom surface of the quartz resonator holder 30 and the quartz resonator holder is positioned to be contacted to an edge of the quartz resonator 10. Accordingly, the temperature dropped due to the Peltier cooler device 20 is transferred to the quartz resonator 10 through the quartz resonator holder 30 so that the temperature of the quartz resonator 10 can be controlled.

In order to transfer effective temperature from the Peltier cooler device 20, the quartz resonator holder 30 may be preferably made of materials with high thermal conductivity, for example, copper.

One surface of the quartz resonator holder 30 may be attached with the platinum resistance temperature sensor 40 to measure the temperature of the quartz resonator holder 30. The temperature of the measured quartz resonator holder 30 is used as an input value of a thermostat 60 connected to the Peltier cooler device 20.

The value input to the thermostat 60 is fedback to control a current output of the thermostat 60 so that temperature of a chill plate in the Peltier cooler device 20 is accurately controlled to be slowly dropped. Slowly dropping the temperature may be performed in the temperature range of 0° C. or less to −60° C. or more.

Also, in order to enable the finer temperature control of the quartz resonator holder 30 in the temperature range of 20° C. to −30° C., heat generated from a bottom surface of the Peltier cooler device 20 can be effectively removed. To this end, a heat sink 50 made of copper where coolant is circulated may be disposed underneath the Peltier cooler device 20.

Preferably, the Peltier cooler device 20 and heat sink 50 is thermal-insulated from a dew-point measurement space so that the change in temperature of the device and the apparatus themselves does not have an effect on the dew-point measurement.

The quartz resonator 10 has a gold electrode surface. The measurement of the resonant frequency of the quartz microbalance dew-point sensor is performed by measuring the resonant frequency of the quartz resonator 10. In order words, if the temperature of the quartz resonator 10 is slowly dropped due to the Peltier cooler device 20 and the quartz resonator holder 30, the temperature of the gold electrode surface of the quartz resonator 10 is dropped. On the gold electrode surface of the quartz resonator 10 applied with alternating current is derived a condensation phenomenon of water molecule so that the change in the resonant frequency of the quartz resonator 10 is measured. In other words, a form that dew begins to form as the temperature of the gold electrode surface of the quartz resonator 10 is dropped and the resonant frequency is reduced from beginning of the formation of dew may be appeared.

In order to effectively measure the temperature forming the dew, the measurement of the resonant frequency is preferably performed at a short time interval, for example, the temperature of the quartz resonator holder 30 and the resonant frequency of the quartz resonator 10 may be measured at a time interval of 0.5 second. The measurement of the resonant frequency may be performed by connecting the frequency measurement circuit line 70, which is connected to the quartz resonator 10, to a frequency counter apparatus located at the outside.

If the temperature is continuously dropped, shock waves are observed at any moment while the reduction of the resonant frequency of the quartz resonator 10 is continued. This means that when the amount of dew formed is increased, the liquid has reached a stage where it cannot be cooperated with the vibration of the quartz resonator 10 due to the inertia according to the weight of the liquid. In other words, when the quartz resonator 10 is vibrated in any one direction, the liquid is not simultaneously moved along with the vibration thereof, i.e., the liquid is not vibrated along with the vibration thereof because of the nature of the liquid intending to move in an existing direction by means of the inertia thereof.

Therefore, the change in the vibration according to the temperature is perturbated so that the graph of the resonant frequency shows an irregularly sudden peak. Consequently, when the peak is observed, it can be judged that the condensation of water molecule formed on the gold electrode of the quartz resonator is the liquid dew and the dew point can be accurately determined in the frequency region where the resonant frequency and shock wave of the quartz crystal microbalance.

Since the frost formed is a solid, the sudden reduction of the resonant frequency is observed. Therefore, whether the dew point is formed or the frost point is formed cannot be accurately grasped only by means of the sudden reduction pattern of the resonant frequency, however, when the perturbation of such a resonant frequency appears, it can be judged to be the dew point and when the shock wave is not observed in the reduction region of the resonant frequency after the condensation of waterdrops is formed, it means that the solid frost is formed. The reason is that in this case, the frost sticks to the gold electrode surface of the quartz resonator so that the inertia effect of the water condensation does not appear, thereby allowing the shock wave pattern not to appear.

The measurement method of frost point, supercooled dew point, and dew point will be described below with reference to FIGS. 2 to 4.

Figure 2:
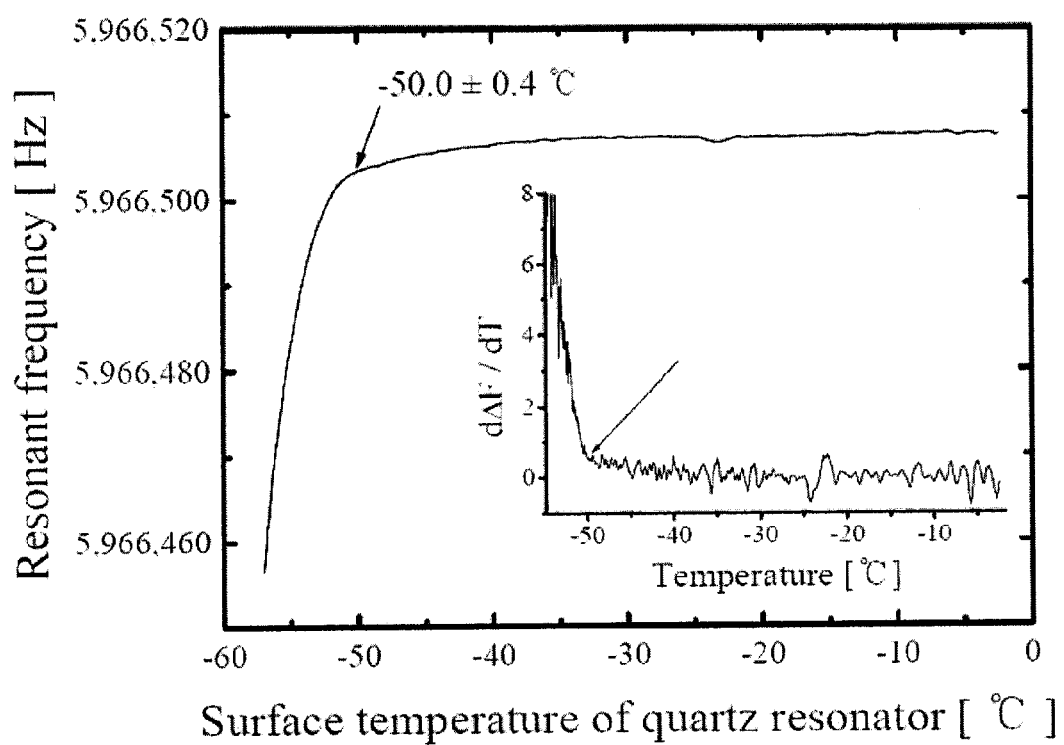
FIG. 2 is a graph showing resonant frequency characteristics according to saturated humid air with respect to an ice of −50° C. to surface temperature of a quartz resonator in accordance with a first embodiment of the present invention.

FIG. 2 is a graph showing resonant frequency characteristics according to saturated humid air with respect to an ice of −50° C. to surface temperature of a quartz resonator in accordance with a first embodiment of the present invention.

Referring to FIG. 2, it can be appreciated that the resonant frequency begins to suddenly reduce from a temperature of −50° C.±0.2° C. or less. The temperature is ice temperature of a saturation bath in a humidity generating apparatus used in the present embodiment. It can be appreciated from this that the temperature is the frost point.

In other words, it means that the state of small waterdrops where the resonant frequency is reduced on the surface of the quartz resonator is the ice. Also, it is shown that that the vibration is continuously and constantly reduced by means of further absorption of water molecule in the air.

The reason is that ice is considered to be rigid so that it can be considered to be moved along with the vibration on the surface of the quartz resonator. When the vibration is constantly reduced, it can be appreciated that a deviation between the surface of the quartz resonator and an interface of an ice layer can be disregarded.

The same tendency is shown when measuring the frost point between −30° C. and −60° C. It can be appreciated from the results that the frost point within the temperature can be measured.

Figure 3:
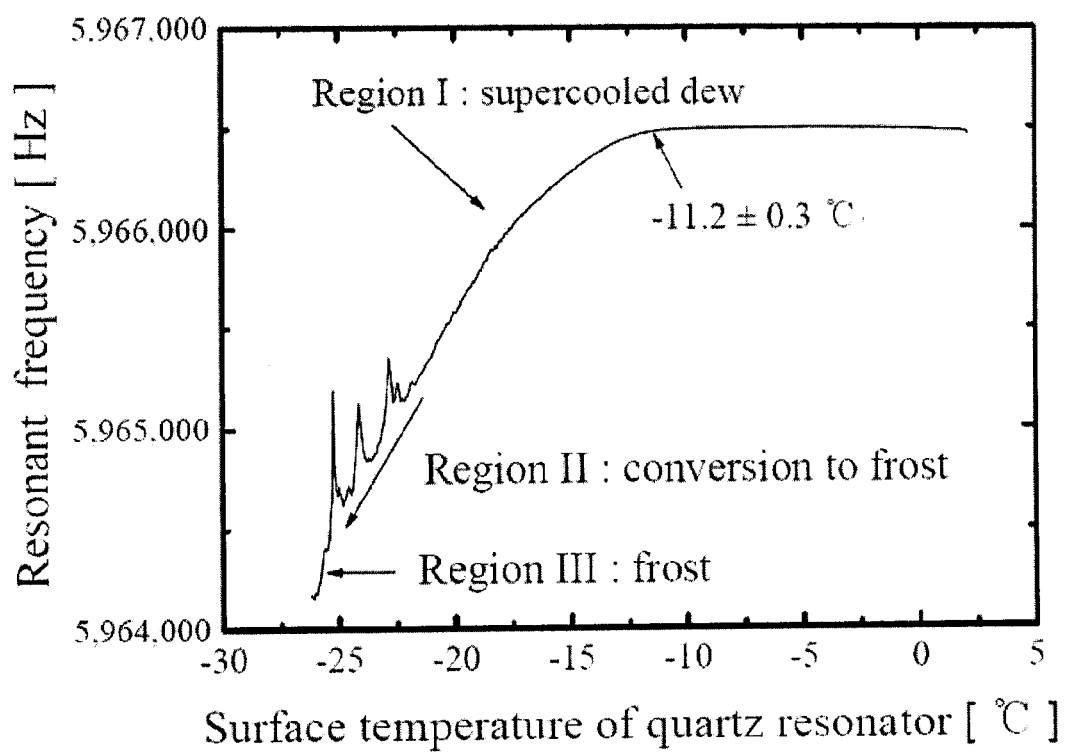
FIG. 3 is a graph showing resonant frequency characteristics according to saturated humid air saturated with respect to an ice of −10° C. to surface temperature of a quartz resonator in accordance with a second embodiment of the present invention.

FIG. 3 is a graph showing resonant frequency characteristics according to a saturated vapor with respect to an ice of −10° C. to the surface temperature of the quartz resonator in accordance with a second embodiment of the present invention, wherein the characteristics of the saturated vapor with the supercooled dew point and the frost point in an interval of 0° C. to −30° C. are shown.

Referring to FIG. 3, the vapor used in the present embodiment is humid air saturated using an ice of −10° C. and vapor partial pressure is 2.597 mbar. Micro waterdrops on the quartz resonator begin to appear at −11.2° C. It can be appreciated that this is not frost but supercooled dew. The reason is that the saturated vapor pressure in the liquid water is about 2.605 mbar at −11.2° C. and the saturated vapor pressure in the ice is 2.335 mbar at −11.2° C. Also, for the liquid water, the saturated vapor pressure has relative uncertainty of 0.3% in the temperature range of −50° C. to 0° C.

In other words, when comparing a numerical difference of the saturated vapor pressure and an analysis error of the dew point/frost point on the curve of the resonant frequency, it can be appreciated that the uncertainty on water of 0° C. or less is associated with the saturated vapor pressure and is not associated with the accuracy of the supercooled dew point measured. Therefore, it can be appreciated that there is no any error or unreasonable in judging the measured temperature to be a liquid state.

It can be appreciated from the curve of the resonant frequency with respect to the surface temperature of the quartz resonator that the shape of the micro waterdrops formed on the surface of the quartz resonator is divided into different three intervals.

In the case of the interval I, the micro waterdrops formed on the surface of the quartz resonator can also be ignored due to its small inertia mass so that the movement of waterdrops is made along with the vibration movement of the surface of the quartz resonator. In other words, although the waterdrops are slipped on the surface of the quartz resonator, it is shorter than the vibration period of the quartz resonator. As shown in the interval I, the resonant frequency shows a tendency to constantly reduce.

In the case of the interval II, the aggregation of the water molecule is continued at the moment that the inertia of the liquid cannot be ignored due to an influence of a liquid size aggregated on the surface of the quartz resonator, so that a sliding phenomenon of the liquid occurs. As a result, the liquid has reached a stage where it cannot be cooperated with the vibration of the quartz resonator 10 due to the inertia according to the weight of the liquid.

As described with reference to FIG. 1, the liquid is not simultaneously moved along with the vibration of the quartz resonator, that is, the liquid is not vibrated along with the quartz resonator because of the nature of the liquid intending to move in the existing direction by means of the inertia thereof so that the sliding phenomenon momentarily occurs, thereby showing the phenomenon that the resonant frequency of the quartz resonator is bounced. When this peak is observed, it can be judged to be the dew point.

In the case of the interval III, since a hopping interval of the resonant frequency disappears and at the same time, constantly reduces again, it can be appreciated that the sliding phenomenon of waterdrops is not shown any more. The dynamical perturbation occurs on the supercooled dew formed on the surface of the quartz resonator according to the rapid vibration movement of the quartz resonator so that phase transition from the supercooled dew to the frost occurs within rapid time. That is, it can be appreciated that the dynamical perturbation accelerates the transition speed.

The transition phenomenon from the supercooled dew to the frost cannot be measured by means of the existing chilled mirror. For example, in the case of the interval II, since the temperature reduction speed is 0.1° C./sec, it can be appreciated that the transition speed is below one minute. Since the speed is the phenomenon that may occur or may not occur over several hours in the chilled mirror being the optical method, the dew point and frost point cannot be accurately distinguished.

Therefore, the present embodiment can accurately distinguish and measure both the frost point and the supercooled dew point by scanning once resonant frequency according to the temperature drop.

Figure 4:
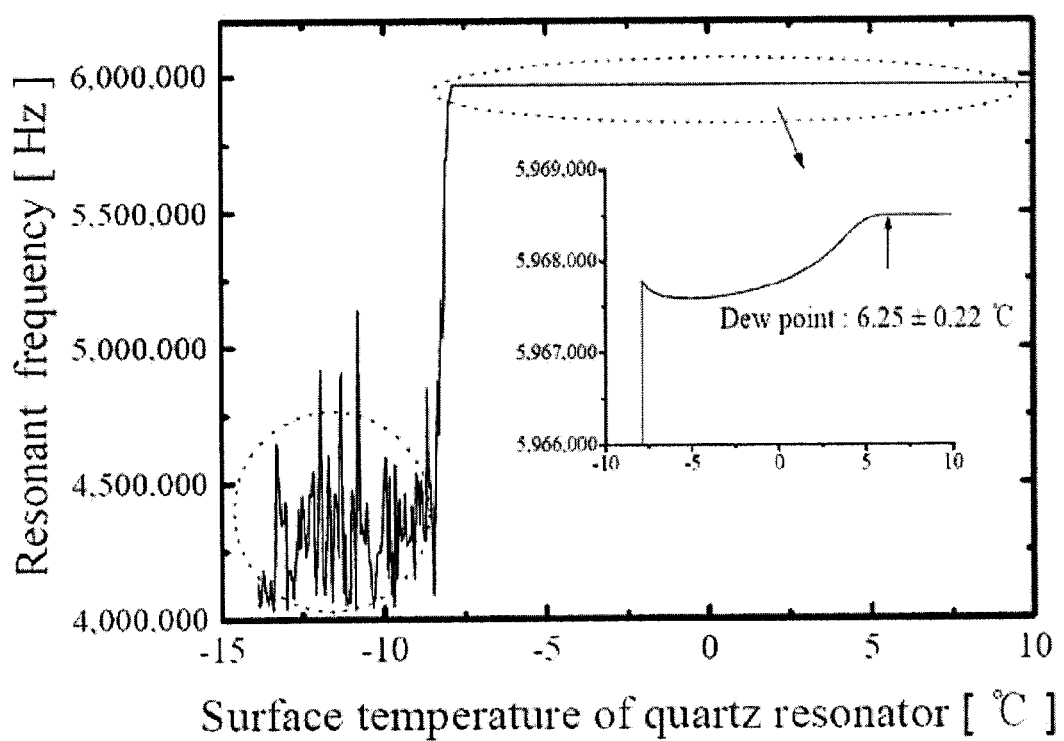
FIG. 4 is a graph showing resonant frequency characteristics according to saturated humid air with respect to water of 6.3° C. to surface temperature of a quartz resonator in accordance with a third embodiment of the present invention.

FIG. 4 is a graph showing the resonant frequency characteristics according to the surface temperature of the quartz resonator with respect to the saturated humid air having the saturated vapor pressure with respect to water of 6.3° C. according to a third embodiment of the present invention.

Referring to FIG. 4, as shown in a graph inserted therein, the condensation temperature of waterdrops is 6.25° C.±0.22° C.

Since this is normal temperature, it can be appreciated that the point observed is the dew point. It can be appreciated that the transition region shown in FIG. 3 does not appear. Since the surface temperature of the quartz resonator is not sufficiently reduced to 0° C. or less, the supercooled dew is not generated. Consequently, it can be analyzed that the transition condition is not formed.

In the case where the dew is generated, it can be appreciated that the sliding phenomenon can be generated by means of the inertia effect of waterdrops, likewise the case where the supercooled dew is formed. As shown in FIG. 4, the reason why the condensation of liquid water is formed on the surface of the quartz resonator and then, the resonant frequency is rapidly reduced is that the aggregation of water molecule is caused due to the high vapor partial pressure in the air to rapidly increase the mass weighted to the quartz resonator. As in a region inside a circular indicated by a dotted line, it can be described that a fluctuation region of the resonant frequency appears since a phase-lock condition of the vibration circuit manufactured for measuring the resonant frequency is destroyed due to the sliding phenomenon of waterdrops and the overload of mass.

[Industrial Applicability]

While the present invention has been described in connection with a limited embodiments and drawings, they are provided only for helping the understandings of the present invention and the present invention is not limited to the disclosed embodiments. Accordingly, it is to be understood that various modifications and changes can be made by those skilled in the art from the above description.

Therefore, the scope of the present invention is not limited to the disclosed embodiments, but is intended to cover various modifications and equivalent arrangements included within the spirit and scope of the appended claims, and equivalents thereof.

The invention claimed is:

1. A measurement method of distinguishing dew and frost point using a quartz crystal microbalance dew-point sensor in low temperature, the method comprises the steps of:
   measuring a resonant frequency of a quartz crystal microbalance dew-point sensor while dropping temperature;
   observing shock waves of the resonant frequency; and
   determining dew point or frost point through the observation of the resonant frequency and shock waves of the quartz crystal microbalance dew-point sensor;
   wherein when observing the resonant frequency of a quartz resonator in the quartz crystal microbalance dew-point sensor while dropping temperature, it is judged that the temperature is the dew point if a transition phenomenon of the shock wave and the resonant frequency is observed in a resonant frequency pattern of the quartz resonator and the temperature is the frost point if the transition phenomenon of the shock wave and the resonant frequency is not observed.

2. The method according to claim 1, wherein before the shock wave of the resonant frequency is observed, the resonant frequency is constantly reduced.

3. The method according to claim 2, wherein after the shock wave of the resonant frequency is observed, the resonant frequency is constantly reduced again.

4. The method according to claim 1, wherein dropping the temperature is performed in the range of 0° C. or less to −90° C. or more.

5. The method according to claim 1, wherein the quartz crystal microbalance dew-point sensor comprises a quartz resonator, a Peltier cooler device, a quartz resonator holder, and a platinum resistance temperature sensor.

6. The method according to claim 5, wherein dropping the temperature is performed by controlling the temperature of the quartz resonator using the Peltier cooler device.

7. The method according to claim 6, wherein the temperature dropped by means of the Peltier cooler device is transferred to the quartz resonator through the quartz resonator holder so that the temperature of the quartz resonator is controlled.

8. The method according to claim 7, wherein the quartz resonator holder is made of copper and one surface of the quartz resonator holder is attached with the platinum resistance temperature sensor to measure the temperature of the quartz resonator holder.

* * * * *

UNITED STATES PATENT AND TRADEMARK OFFICE
CERTIFICATE OF CORRECTION

PATENT NO.      : 8,485,720 B2
APPLICATION NO. : 12/747320
DATED           : July 16, 2013
INVENTOR(S)     : Kwon et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this
Eighth Day of September, 2015

Michelle K. Lee
*Director of the United States Patent and Trademark Office*